United States Patent
Cui et al.

(10) Patent No.: US 12,158,469 B2
(45) Date of Patent: Dec. 3, 2024

(54) SYNTHETIC PEPTIDE FOR DETECTING HIV-1

(71) Applicant: Fapon Biotech Inc., Shenzhen (CN)

(72) Inventors: Peng Cui, Shenzhen (CN); Zhiqiang He, Shenzhen (CN); Yuan Meng, Shenzhen (CN)

(73) Assignee: Fapon Biotech Inc., Shenzhen (CN)

( * ) Notice: Subject to any disclaimer, the term of this patent is extended or adjusted under 35 U.S.C. 154(b) by 975 days.

(21) Appl. No.: 17/264,984

(22) PCT Filed: Aug. 6, 2019

(86) PCT No.: PCT/CN2019/099503
§ 371 (c)(1),
(2) Date: Feb. 1, 2021

(87) PCT Pub. No.: WO2020/029972
PCT Pub. Date: Feb. 13, 2020

(65) Prior Publication Data
US 2021/0172951 A1 Jun. 10, 2021

(30) Foreign Application Priority Data
Aug. 9, 2018 (CN) .............. 201810904120

(51) Int. Cl.
C07K 14/00 (2006.01)
G01N 33/569 (2006.01)
G01N 33/68 (2006.01)

(52) U.S. Cl.
CPC ..... *G01N 33/56988* (2013.01); *C07K 14/001* (2013.01); *G01N 33/6854* (2013.01); *G01N 2333/16* (2013.01); *G01N 2469/20* (2013.01)

(58) Field of Classification Search
CPC .................................................. C07K 14/001
See application file for complete search history.

(56) References Cited

U.S. PATENT DOCUMENTS

| | | | |
|---|---|---|---|
| 5,763,160 A | 6/1998 | Wang | |
| 5,830,634 A | 11/1998 | Brust et al. | |
| 6,399,294 B1 | 6/2002 | Charneau et al. | |
| 2003/0082521 A1 | 5/2003 | Brasseur et al. | |
| 2004/0141996 A1* | 7/2004 | Gelder ............... | C07K 16/1063 435/5 |

FOREIGN PATENT DOCUMENTS

| | | | |
|---|---|---|---|
| CN | 1195702 A | | 10/1998 |
| CN | 1263536 A | | 8/2000 |
| CN | 108997482 A | * | 12/2014 |
| CN | 106883300 A | | 6/2017 |
| CN | 107090019 A | | 8/2017 |
| CN | 107922474 A | | 4/2018 |
| CN | 106632691 A | | 3/2020 |
| WO | WO2002/053587 A2 | | 7/2002 |
| WO | WO2011/077093 A1 | | 6/2011 |
| WO | WO2013127288 A1 | | 9/2013 |
| WO | WO2016/171980 A1 | | 10/2016 |
| WO | WO2017139392 A1 | * | 8/2017 |

OTHER PUBLICATIONS

Bork. Powers and Pitfalls in Sequence Analysis: The 70% Hurdle. Genome Research, 2000, 10:398-400 (Year: 2000).*
Greenspan et al. 1999. Defining epitopes: It's not as easy as it seems; Nature Biotechnology, 17:936-937 (Year: 1999).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine ResidueJ. Cell Biol. 111:2129-2138, 1990 (Year: 1990).*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Canadian Office Action Mailed Jan. 31, 2022 for CA Application No. 3,108,832 "Synthetic Peptide for Detecting HIV-1", Cui et al.. 3 pages.
Chinese Office Action mailed Jan. 7, 2022 for CN Application No. 201810904120.2 "Synthetic Peptide for Detecting HIV-1", Cui et al.. 10 pages.
European Search Report dated Oct. 27, 2021 in European Application No. 19848226.7, a foreign corresponding application of U.S. Appl. No. 17/264,984, 7 pages.
Shiko et al., "Env Polyprotein," Jun. 2001, XP055852222, retrieved from EBI Database Accession No. Q99IB9, 2 pages.
Korean Office Action dated Jun. 19, 2023 in Korean Appliction No. 10-2021-7003738, a corresponding foreign application of U.S. Appl. No. 17/264,984, 14 pages.
International Search Report and Written Opinion dated Nov. 4, 2019 in Internatioanl Application No. PCT/CN2019/099503, 13 pps.
Zhai, Jian-xin, et al., "Rapid and Simultaneous Detection of IgG Antibodies to HIV-1 and HIV-2 by Dot Immunogold Filtration Assay," Mar. 2006. Virologica Sinica, 21(2): 116-120.
Canadian Office Action mailed Nov. 30, 2022 for Canadian Application No. 3,108,832, a foreign counterpart to U.S. Appl. No. 17/264,984, 4 pages.
Chinese Office Action mailed Aug. 30, 2022 for Chinese Application No. 202210287310.0, a foreign counterpart to U.S. Appl. No. 17/264,984, 12 pages.
Chinese Office Action mailed May 28, 2021 for CN Application No. 201810904120.2 "Synthetic Peptide for Detecting HIV-1", Cui et al.. 12 pages.
Chinese Office Action mailed Jul. 9, 2021 for CN Application No. 201810904120.2 "Synthetic Peptide for Detecting HIV-1", Cui et al.. 12 pages.

(Continued)

*Primary Examiner* — Prema M Mertz
(74) *Attorney, Agent, or Firm* — Lee & Hayes, P.C.

(57) ABSTRACT

The present disclosure relates to the field of medical diagnosis, and specifically, relates to a synthetic peptide for detecting HIV-1. The synthetic peptide is obtained by mutating the amino acid sequence set forth as SEQ ID NO: 1. The synthetic peptide can better detect anti-HIV-1 antibodies, and can better avoid potential "false negative" and "false positive" results.

13 Claims, No Drawings
Specification includes a Sequence Listing.

(56) References Cited

OTHER PUBLICATIONS

Kirschman et al., "HIV-1 Envelope Glycoprotein Trafficking through the Endosomal Recycling Compartment is Required for Particle Incorportation," Dec. 2017. Journal of Virology, 92(5): e01893-17, 47 pages.

Xin et al., "HIV-1 Gp41 Recombinant Antigen: Expression and Immunoreactivity Analysis," 2012 Modern Immunology. 32(3):230-233.

* cited by examiner

SYNTHETIC PEPTIDE FOR DETECTING HIV-1

CROSS-REFERENCE TO RELATED APPLICATIONS

The present application is a U.S. National Phase Application of International Application No. PCT/CN2019/099503, filed Aug. 6, 2019, which claims priority to Chinese Patent Application No. 201810904120.2, titled "Synthetic Peptide for Detecting HIV-1", filed on Aug. 9, 2018 in the China Patent Office, both of which are hereby incorporated by reference in their entirety.

TECHNICAL FIELD

The present disclosure relates to the field of medical diagnosis, and particularly, to a synthetic peptide for detecting HIV-1.

BACKGROUND

Human Immunodeficiency Virus (HIV), which causes Acquired Immune Deficiency Syndrome (AIDS), was first discovered in the 1980s and has spread throughout the world. According to the report from the World Health Organization, as of the end of 2016, there were approximately 36.7 million HIV-infected patients. As of Jun. 30, 2017, there were 718,000 HIV-infected patients or AIDS patients in China. HIV mainly attacks the human body's helper T lymphocyte system, selectively invades cells with CD4 molecules, and destroys the body's immune function, causing the immune system to lose resistance, accompanying with severe opportunistic infections, which leads to various diseases and cancers survival in the body and finally leads to AIDS. Since no effective drugs and vaccines are available to treat or prevent AIDS till now, HIV infection has become the most serious infectious disease and public health problem in the world nowadays.

HIV virus is an RNA retrovirus with a lipid envelope, and its single copy gene RNA is approximately 9.2 Kb to 9.8 Kb in length. HIV includes three main structural genes: env, gag, and pol, which respectively encode proteins that produce different functions, i.e., antigens. When HIV has invaded the body, antibodies are usually produced in about 6 weeks. HIV precursor P55 antibody and core protein P24 antibody will first appear in the serum, following by outer envelope protein GP120 antibody and transmembrane glycoprotein gp41 antibody. Currently, HIV is mainly found in HIV-1 and HIV-2, and four HIV strains including M, N, O, and P are known. Among them, M and N are the most widely spread. Only two P-type cases were found in the world so far, and there are only 100,000 O-type cases, mainly in West and Central Africa. These types are very similar in biological characteristics, and their genomes share 40%-50% homology. In China, the HIV-1 is the prevalent type at present.

As the HIV antigen and nucleic acid testing requires equipment, reagents, and labor that cause excessive cost, HIV antibody testing is still dominating the HIV testing market. At present, HIV antibody detection materials are developing, on the one hand, in the direction of improving sensitivity and specificity as well as shortening the window period, and on the other hand, in the direction of convenience and efficiency. In order to comply with the above development trends, it is urgent in this field to provide HIV-1 recombinant proteins that can be applied to HIV-1 antibody testing.

SUMMARY

The present disclosure relates generally to methods and substances for diagnosing human immunodeficiency virus (HIV) infection, and more particularly, the present disclosure relates to a synthetic peptide having reactinogenicity of binding to HIV-1 type antibodies, and uses thereof. The objectives of the present disclosure include, for example, providing a means for diagnostic laboratories, specifically providing a specific peptide, which allows better detection of anti-HIV-1 antibody and avoids potential "false negatives" and "false positive" results.

The present disclosure provides a synthetic peptide. The synthetic peptide is an amino acid sequence set forth as SEQ ID NO: 1 containing a mutation site. The mutation site is selected from at least one of:

T77, replaced by V, N or S;
N101, replaced by D, E or Q;
G105, replaced by K, H or R;
P124, replaced by D or E;
K127, replaced by D, E or Q.

Alternatively, the synthetic peptide is an amino acid sequence having at least 80% sequence identity with any one of the above sequences, and having a sensitivity greater than 99% and/or a specificity greater than 99.4%.

By virtue of the one or more amino acid mutation sites, the synthetic peptide provided by the present disclosure can have a sensitivity of 100%, and a specificity greater than 99.75%, when compared with the prior art.

DESCRIPTION OF EMBODIMENTS

To clarify objectives, technical solutions, and advantages of embodiments of the present disclosure, the technical solutions in the embodiments of the present disclosure will be described clearly and in detail below. The conventional conditions or the conditions recommended by the manufacturers are adopted where the specific conditions are not specified in the embodiments. The reagents or instruments are all conventional products that can be obtained through commercial purchase where the used reagents or instruments without an indication of the manufacturer.

Scientific and technical terms used in the present disclosure shall have the meanings that those skilled in the art commonly understand, unless otherwise defined herein. Examples of methods and material are described below, but the methods and materials similar or equivalent to those described herein can also be used in the present disclosure.

The present disclosure relates to a synthetic peptide, which is an amino acid sequence set forth as SEQ ID NO: 1 containing a mutation site.

The mutation site is selected from one, two, three, four, or five of the following mutation sites:

T77, replaced by V, N or S;
N101, replaced by D, E or Q;
G105, replaced by K, H or R;
P124, replaced by D or E;
K127, replaced by D, E or Q; or Alternatively, the synthetic peptide is an amino acid sequence having at least 80%, 85%, 88%, 89%, 90%, 91%, 92%, 93%, 94%, 95%, 96%, 97%, 98%, 99%, or 99.5% sequence identity with any one of the above sequences.

In some embodiments, the synthetic peptide, kit or detection method provided by the present disclosure have a sensitivity greater than 99%, greater than 99.1%, greater than 99.2%, greater than 99.3%, greater than 99.4%, greater than 99.5%, greater than 99.6%, greater than 99.7%, greater than 99.8%, or greater than 99.9%.

In some embodiments, the synthetic peptide, kit or detection method provided by the present disclosure have a specificity greater than 99.4% (such as 99.5% or more, 99.6% or more, 99.7% or more, 99.8% or more, 99.9% or more).

The above sensitivity and specificity are determined based on experiments in examples of the present disclosure.

In the early stage of HIV-1 infection, subjects, for example, mammals such as humans, have lower HIV-1 antibody levels in biological samples and are therefore not easily detected. Since a detection method using the synthetic peptide of the present disclosure has higher sensitivity and specificity than the detection methods known in the prior art, the synthetic peptide of the present disclosure is more suitable for detecting or diagnosing the early stage of HIV-1 infection and/or the early stage of AIDS than those known in the prior art.

In one or more embodiments, the present disclosure provides a polypeptide containing all or a part of the sequence set forth as SEQ ID NO: 1, for example, at least 30 consecutive amino acids.

The synthetic peptide provided by the present disclosure is subjected to, for example, purification treatment, and is particularly suitable for the identification and/or enrichment of HIV-1 type viruses in animals, particularly mammals, more particularly primates, and especially humans. HIV-1 retrovirus is the most common, and dominates in many regions of the world.

In one or more embodiments, the mutation site includes: T77, replaced with V, N or S.

In one or more embodiments, the mutation site includes: N101, replaced by D, E or Q.

In one or more embodiments, the mutation site includes: G105, replaced by K, H or R.

In one or more embodiments, the mutation site includes: P124, replaced by D or E.

In one or more embodiments, the mutation site includes: K127, replaced by D, E or Q.

In one or more embodiments, the mutation site further includes one, two, three, four, or five of the following mutation sites:
R18, replaced by S;
Q95, replaced by E;
L106, replaced by E;
L123, replaced by K;
N130, replaced by K.

In one or more embodiments, the mutation site includes: R18, replaced by S.

In one or more embodiments, the mutation site includes: Q95, replaced by E.

In one or more embodiments, the mutation site includes: L106, replaced by E.

In one or more embodiments, the mutation site includes: L123, replaced by K.

In one or more embodiments, the mutation site includes: N130, replaced by K.

In one or more embodiments, the mutation site is:
R18, replaced by S; T77, replaced by V, N or S; Q95, replaced by E; N101, replaced by D, E or Q; G105, replaced by K, H or R; L106, replaced by E; L123, replaced by K; P124, replaced by D or E; K127, replaced by D, E or Q; N130, replaced by K.

In one or more embodiments, the mutation site is:
T77, replaced by V; Q95, replaced by E or unreplaced; N101, replaced by D, E or Q; G105, replaced by K, H or R; L106, replaced by E or unreplaced; P124, replaced by D or E; K127, replaced by D, E or Q.

In one or more embodiments, the mutation site is: R18, replaced by S or unreplaced; T77, replaced by V, N or S; Q95, replaced by E or unreplaced; N101, replaced by D, E or Q; G105, replaced by K, H or R; L106, replaced by E or unreplaced; L123, replaced by K or unreplaced; P124, replaced by D or E; K127, replaced by D, E or Q; N130, replaced by K or unreplaced.

In one or more embodiments, the mutation site is: R18, replaced by S; T77, replaced by S; Q95, replaced by E or unreplaced; N101, replaced by D, E or Q; G105, replaced by K, H or R; L106, replaced by E or unreplaced; L123, replaced by K; P124, replaced by D; K127, replaced by D, E or Q; N130, replaced by K.

In one or more embodiments, the synthetic peptide is labeled with an indicator for displaying signal strength.

In one or more embodiments, the indicator for displaying signal strength includes any one of fluorescent substance, quantum dot, digoxigenin-labeled probe, biotin, radioisotope, radioactive contrast agent, paramagnetic ion fluorescent microsphere, electron dense substance, chemiluminescent label, ultrasound contrast agent, photosensitizer, colloidal gold, or enzyme.

In one or more embodiments, the present disclosure provides a product including the synthetic peptide, such as a microtiter plate (on which the synthetic peptide can be coated).

The present disclosure further relates to an isolated nucleic acid molecule encoding the synthetic peptide as described above.

The present disclosure further relates to a vector including a nucleic acid molecule as described above.

The present disclosure further relates to a host cell transformed with a vector as described above.

The host cell may be a eukaryotic cell, such as a mammalian cell.

The present disclosure further relates to a method for producing the synthetic peptide as described above, including:
a) expressing the nucleic acid molecule as described above; or
b) chemical synthesis, adding amino acids to obtain a complete polypeptide.

Through the method of a) synthesis described above, the expressed polypeptide can be enriched by the well-known affinity purification.

The chemical synthesis can be performed in equipment known to those skilled in the art, for example, an automatic peptide synthesizer, such as an automatic peptide synthesizer sold by Applied BioSystems and the like, and the polypeptide can be obtained by peptide synthesis.

The present disclosure further relates to a modified synthetic peptide, which is obtained by labeling the synthetic peptide described above with an indicator for displaying signal strength.

In one or more embodiments, the indicator for displaying signal strength includes any one of fluorescent substance, quantum dot, digoxigenin-labeled probe, biotin, radioisotope, radioactive contrast agent, paramagnetic ion fluorescent microsphere, electron dense substance, chemiluminescent label, ultrasound contrast agent, photosensitizer, colloidal gold, or enzyme.

In one or more embodiments, the fluorescent substance includes any one of: Alexa 350, Alexa 405, Alexa 430, Alexa 488, Alexa 555, Alexa 647, AMCA, amino acridine, BODIPY 630/650, BODIPY 650/665, BODIPY-FL, BODIPY-R6G, BODIPY-T MR, BODIPY-TRX, 5-carboxy-4',5'-dichloro-2',7'-dimethoxyfluorescein, 5-carboxy-2',4',5',7'-tetrachlorofluorescein, 5-carboxyfluorescein, 5-carboxyrhodamine, 6-carboxyrhodamine, 6-carboxytetramethylrhodamine, Cascade Blue, Cy2, Cy3, Cy5, Cy7, 6-FAM, dansyl chloride, fluorescein, HEX, 6-JOE, NBD (7-nitrobenzo-2-oxo-1,3-diazole), Oregon Green 488, Oregon Green 500, Oregon Green 514, Pacific Blue, phthalic acid, terephthalic acid, isophthalic acid, Cresol Fast Violet, Cresol Blue Violet, Brilliant Cresyl Blue, p-aminobenzoic acid, erythrosine, phthalocyanine, azomethine, cyanine, xanthine, succinyl fluorescein, rare earth metal cryptate, europium tribipyridyl diamine, europium cryptate or chelate, diamine, biscyanine, La Jolla blue dye, allophycocyanin, allococyanin B, phycocyanin C, phycocyanin R, thiamine, phycoerythrin, phycoerythrin R, REG, rhodamine green, rhodamine isothiocyanate, rhodamine red, ROX, TAMRA, TET, tetramethylrhodamine isothiol (TRIT), tetramethylrhodamine, and Texas Red.

In one or more embodiments, the radioisotope includes any one of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{9}$mTc, $^{94}$Tc, $^{99}$mTc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb, and $^{83}$Sr.

In one or more embodiments, the enzyme includes any one of horseradish peroxidase, alkaline phosphatase, and glucose oxidase.

In one or more embodiments, the fluorescent microsphere is polystyrene fluorescent microsphere, coated with rare earth fluorescent ion europium inside.

The present disclosure further relates to a kit including a synthetic peptide as described above, or a modified synthetic peptide as described above.

In one or more embodiments, the kit further includes one or more of an immunologically acceptable diluent, a buffer, a protease inhibitor, a blocking agent for blocking non-specific binding of antibodies, or a second antibody having an affinity for HIV-1 antibody.

In one or more embodiments, the protease inhibitor may include one or more of PMSF, EDTA, NaN3, pepstantin, leupeptin, aprotinin, Indinavir, Ritonavir, Nelfinavir, Amprenavir, or Kaletra.

In one or more embodiments, the second antibody having an affinity for the HIV-1 antibody may be an antibody against human Fc segment, and the species may be mouse, rat, rabbit, dog, sheep, horse, or human.

In one or more embodiments, the second antibody having an affinity for the HIV-1 antibody is labeled with an indicator for displaying signal strength.

In one or more embodiments, the blocking agent for blocking non-specific binding of antibodies includes BSA, FBS.

In one or more embodiments, the buffer is phosphate buffer (PBS), Tris salt buffer (TBS), Tris salt buffer-Tween (TBST), or Tris salt buffer-Triton (TBST).

In one or more embodiments, the kit further includes, for example, the microtiter plate described above.

In one or more embodiments, when the kit includes the modified synthetic peptide described above, the kit further includes a reagent for detecting the indication for displaying signal strength.

The reagent for detecting the indication for displaying signal strength is one of those well known to those skilled in the art. As an example, when the indicator is horseradish peroxidase (HRP), the corresponding reagent can be selected from hydrogen peroxide and luminol; and when the indicator is biotin, the corresponding reagent can be selected from avidin, and so on.

The present disclosure further relates to a method for detecting anti-HIV-1 antibody, which includes: forming an immune complex by contacting a biological sample with the synthetic peptide as described above, or the modified synthetic peptide as described above, or reagents in the kit as described above.

As used herein, the term "detection/detecting" means quantitatively or qualitatively detecting a target molecule in a sample to be studied. For example, the presence or level of anti-HIV-1 antibodies in a biological sample is quantitatively or qualitatively detected.

The presence of the synthetic peptide or the modified synthetic peptide in the immune complex is detected to indicate the presence of HIV-1 antibodies in the biological sample.

The method is performed in vivo or in vitro for diagnostic or non-diagnostic purposes.

As used herein, the term "diagnosis" or "medical diagnosis" refers to the judgment of a person's mental and physical state from a medical perspective. Specifically, it is a process of determining which disease or condition can explain a subject's symptoms and signs. For example, the HIV-1 infection or the presence of AIDS in a subject is determined by using a synthetic peptide described herein.

The present disclosure further relates to a use of the synthetic peptide described above, or the modified synthetic peptide described above, or the kit described above in a preparation of an HIV-1 diagnostic agent.

In some embodiments, the present disclosure provide a method for obtaining or designing recombinant proteins for detecting HIV. The method may include one or more of the following steps:

selecting human immunodeficiency virus envelope protein, selecting a segment of the protein, and performing mutation design at some sites thereof, where the corresponding recombinant proteins are prepared by expression purification, and the recombinant proteins having high activity and specificity are obtained through activity and specific screening;

synthesizing sequence fragments and ligating them to a vector such as pMD18-T vector to construct a T vector containing the target fragment;

constructing, through site-directed mutation design, a vector containing a specific mutation target fragment, such as the pMD18-T vector;

preparation method of the recombinant protein: designing an upstream primer (for example, with EcoR I restriction site) and a downstream primer (for example, with BamH I restriction site), using the vector containing the target fragment as a template to amplify the target gene, which is ligated to a vector such as pET-28a after double digestion and purification, and transforming cells such as E. coli BL21; after screening for positive clones, picking a single colony and inoculating it into a medium such as LB medium containing 50 μl/ml of Kan; and shaking and incubating at a temperature of 37° C.; after the OD600 reaches 0.6-0.8, adding 1.0 mM of IPTG, performing inducing culture at 37° C. for 2-4 hours, extracting the total protein, and identifying the expression of the recombinant protein by SDS-PAGE; performing the first purification of the target protein using NI ion chelating column, performing the second purification of the target protein using SP column, and identifying the purity of the recombinant protein by SDS-PAGE.

The present disclosure further provides a method for diagnosing HIV-1 related diseases. The method includes:

forming an immune complex by contacting a biological sample with the synthetic peptide described above, or the modified synthetic peptide described above, or reagents in the kit described above; and detecting a presence of the synthetic peptide or the modified synthetic peptide in the immune complex to indicate a presence of HIV-1 antibody in the biological sample.

In one or more embodiments, the HIV-1 related disease is HIV-1 infection or AIDS.

In one or more embodiments, the HIV-1 related disease is HIV-1 infection at an early stage or AIDS at an early stage.

In one or more embodiments, the biological sample is collected from a mammal, such as a human.

In one or more embodiments, the biological sample includes at least one of blood, serum, plasma, cell culture supernatant, saliva, cerebrospinal fluid, semen, prostate fluid, tissue, or tissue lysate.

The present disclosure further provides a use of the synthetic peptide described above, or the modified synthetic peptide described above, or the kit described above in diagnosing HIV-1.

Though the one or more amino acid mutation sites, the synthetic peptide provided by the present disclosure can have a sensitivity of 100%, and a specificity greater than 99.75%, when compared with the prior art.

The embodiments of the present disclosure are described in detail in combination with the following examples. Those skilled in the art can understand that, the following examples are merely for the purpose of explaining the present disclosure, but are not intended to limit the present disclosure. The conventional conditions or the conditions recommended by the manufacturers are adopted where the specific conditions are not specified in the examples. The reagents or instruments are all conventional products that can be obtained through commercial purchase where the used reagents or instruments without an indication of the manufacturer.

Example 1

Design of Recombinant Proteins

The gene sequence encoding SEQ ID NO: 1 was synthesized by gene synthesis, and the amino acids at sites, including X77 (X77 represents the 77-th site of the sequence set forth as SEQ ID NO: 1, the same applies hereinafter), X95, X101, X105, X106, X124, and X127, were subjected to mutation designs.

The amino acid at site X77 was mutated from T to V, or N, or S. The amino acid at site X95 was mutated from Q to E. The amino acid at site X101 was mutated from N to E, or D, or Q. The amino acid at site X105 was mutated from G to K, or H, or R. The amino acid at site X106 was mutated from L to E. The amino acid at site X124 was mutated from P to D, or E. The amino acid at site X127 was mutated from K to D, or E, or Q.

The mutant clones were constructed based on the above mutation manners, the options include:

X77, X101, X105, X124, and X127 are respectively

V, E, K, D and D, named as HIV-Ag-1;
N, D, H, E, and E, named as HIV-Ag-2;
S, Q, R, D, and Q, named as HIV-Ag-3;
S, D, R, E, and E, named as HIV-Ag-4;
V, D, K, E, and D, named as HIV-Ag-5;
N, E, H, D, and E, named as HIV-Ag-6;
V, Q, R, D, and Q, named as HIV-Ag-7;
S, Q, K, E, and D, named as HIV-Ag-8;
N, Q, H, E, and Q, named as HIV-Ag-9.

The mutant clones were constructed into the pMD18-T vector (TaKara Bio, Dalian, catalog number: 6011). The clone of gene sequence of SEQ ID NO: 1 was constructed and named as pMD18-T-HIV-Ag-0, and the mutant clones were named as pMD18-T-HIV-Ag-1 to pMD18-T-HIV-Ag-9 for subsequent amplification and nucleic acid fragment preservation.

Example 2

Design of Recombinant Proteins

Based on Example 1, the amino acids of sequences X18, X95, X106, X123, and X130 in HIV-Ag-1 to HIV-Ag-9 were subjected to mutation design.

The amino acid R at site X18 is mutated to S. The amino acid at site X95 is mutated from Q to E. The amino acid at site X106 is mutated from L to E. The amino acid at site X123 is mutated from L to K. The amino acid at site X130 is mutated from N to K. The new sequences were named as HIV-Ag-10 to HIV-Ag-18, and they were constructed into the pMD18-T vector and named as pMD18-T-HIV-Ag-10 to pMD18-T-HIV-Ag-18 for subsequent amplification and nucleic acid fragment preservation.

Example 3

Construction, Inducible Expression and Purification of Recombinant Protein Expression Vectors Construction and inducible expression of recombinant protein expression vectors: a upstream primer (with EcoR I restriction site) and a downstream primer (with BamH I restriction site) were designed, pMD18-T-HIV-Ag-0 to pMD18-T-HIV-Ag-18 were used as templates to amplify the target gene. The target gene, after purification, was digested with EcoR I (TaKara Bio, Dalian, catalog number: 1010A) and BamH I restriction enzyme (TaKara Bio, Dalian, catalog number: 1040A) for double digestion and incubated at 37° C. for 2 h. The purified and digested product was ligated with the vector pET-28a subjected to the same digestion, and incubated at 22° C. for 2 hours and at 16° C. for 2 hours. The ligated product was transformed into E. coli BL21 competence (New England Biolabs ((NEB)), catalog number: C2530H) by heat shock, and spread on an LB plate containing 50 µg/ml of Kan, and cultured at 37° C. for 16 hours. The positive clones were picked and identified with bacterial liquid by PCR, and then sent for sequencing after double enzyme digestion. The positively mono-cloned clones with correct sequencing were selected and inoculated into LB medium containing 50 µg/ml of Kan and cultured at 37° C. with shaking. After the OD600 reached 0.6-0.8, 1.0 mM of IPTG was added and induced to culture at 37° C. for 2-4 hours. The total protein was extracted and the expression of the recombinant protein was identified by SDS-PAGE. By means of 6*HIS tag on the N-terminus of the recombinant protein, the proteins were purified through nickel ion chelating purification and SP column purification to reach a purity of 96%. The obtained proteins were named as HIV-Ag-0 to HIV-Ag-18, respectively.

Example 4

Application of Mutant Clones HIV-Ag-1 to HIV-Ag-9 Recombinant Antigens in Enzyme Immunity Product Process and Evaluation of their Activity and Specificity The enzyme immunoassay was performed as follows:
Coating: the recombinant proteins were added to a coating solution of 50 mM of CB (PH=9.6) at a working concentration of 100 ng/ml and mixed, and then the mixture was added to a polystyrene plate in 100 µl per well, performing coating at 4° C. for 18-20 hours.

Blocking: the coated plate was taken out and equilibrated at room temperature for 30 min, the plate was washed twice with washing solution, 150 μl blocking solution was added into each well, performing the blocking at 37° C. for 2 hours. The plate was patted to dry, and placed into an electronic drying box with humidity less than 30% and dried for 24 hours before use.

Labeling: the recombinant proteins were labeled with HRP at 50 ng/ml in a recommended manner, and diluted with an enzyme working solution and then mixed (enzyme diluent: 20 mM PB; 150 mM NaCl; 0.5% BSA; 0.05% Tween-200; 0.1% P300).

Reaction mode and reaction time: 50 μl sample to be tested+50 μl sample diluent reacted at 37° C. for 60 min; the plate was washed 5 times and patted to dry, then 100 μl of labeled recombinant protein-HRP working solution was added, and the mixture reacted at 37° C. for 30 min; the plate was washed 5 times, 50 μl of developer A and 50 μl of developer B were added to develop color for 30 min; 50 μl of stop buffer was added and dual-wavelength detection was performed at wavelengths of 450 nm and 630 nm, and the testing was read within 10 min.

For the comparison experiments with commercial kits, 500 HIV-1 positive serums and 3,000 HIV-1 antibody negative serums were tested. The results are shown in Table 1. The recombinant proteins of the present disclosure were used for HIV-1 antibody detection, the sensitivity was improved, and the specificity was significantly improved and superior to existing products.

TABLE 1

Test results after mutation

|  | 500 HIV-1 positive serums (sensitivity) | 3,000 HIV-1 antibody negative serums (specificity/false positive rate) |
|---|---|---|
| Control reagent (commercially available) | 499 (99.8%) | 18 (99.40%/0.60%) |
| HIV-Ag-0 | 498 (99.6%) | 24 (99.20%/0.80%) |
| HIV-Ag-1 | 500 (100%) | 6 (99.80%/0.20%) |
| HIV-Ag-2 | 500 (100%) | 8 (99.76%/0.24%) |
| HIV-Ag-3 | 500 (100%) | 8 (99.76%/0.24%) |
| HIV-Ag-4 | 500 (100%) | 5 (99.83%/0.17%) |
| HIV-Ag-5 | 500 (100%) | 7 (99.87%/0.13%) |
| HIV-Ag-6 | 500 (100%) | 6 (99.80%/0.20%) |
| HIV-Ag-7 | 500 (100%) | 7 (99.75%/0.25%) |
| HIV-Ag-8 | 500 (100%) | 9 (99.79%/0.21%) |
| HIV-Ag-9 | 500 (100%) | 9 (99.79%/0.21%) |

Example 5

Activity Evaluation of Mutant Clones HIV-Ag-1 to HIV-Ag-18 Recombinant Antigens in Enzyme Immunization Process The enzyme immunoassay was performed as follows:

Coating: the recombinant proteins were added to a coating solution of 50 mM of CB (PH=9.6) at a working concentration of 100 ng/ml and mixed, and then the mixture was added to a polystyrene plate in 100 μl per well, performing coating at 4° C. for 18-20 hours.

Blocking: the coated plate was taken out and equilibrated at room temperature for 30 min, the plate was washed twice with washing solution, 150 μl blocking solution was added into each well, performing the blocking at 37° C. for 2 hours. The plate was patted to dry, and placed into an electronic drying box with humidity less than 30% and dried for 24 hours before use.

Labeling: the recombinant proteins were labeled with HRP at 50 ng/ml in a recommended manner, and diluted with an enzyme working solution and then mixed (enzyme diluent formula: 20 mM PB; 150 mM NaCl; 0.5% BSA; 0.05% Tween-200; 0.1% P300).

Reaction mode and reaction time: 50 μl sample to be tested+50 μl sample diluent reacted at 37° C. for 60 min; the plate was washed 5 times and patted to dry, then 100 μl of labeled recombinant protein-HRP working solution was added, and the mixture reacted at 37° C. for 30 min; the plate was washed 5 times, 50 μl of developer A and 50 μl of developer B were added to develop color for 30 min; 50 μl of stop buffer was added and dual-wavelength detection was performed at wavelengths of 450 nm and 630 nm, and the testing was read within 10 min.

500 HIV-1 positive serums, each diluted with a sample diluent at 1: 200, served as test samples for activity testing. The results are shown in Table 2. After mutation, the average sensitivity of the 500 positive samples after dilution was significantly improved.

TABLE 2

Test results after mutation

| Clone Name | Average OD600 readings of 500 HIV samples, each diluted at 1:200 |
|---|---|
| HIV-Ag-1 | 0.732 |
| HIV-Ag-10 | 0.856 |
| HIV-Ag-2 | 0.794 |
| HIV-Ag-11 | 1.122 |
| HIV-Ag-3 | 0.642 |
| HIV-Ag-12 | 0.989 |
| HIV-Ag-4 | 1.254 |
| HIV-Ag-13 | 1.261 |
| HIV-Ag-5 | 0.901 |
| HIV-Ag-14 | 1.101 |
| HIV-Ag-6 | 1.264 |
| HIV-Ag-15 | 1.367 |
| HIV-Ag-7 | 0.892 |
| HIV-Ag-16 | 1.299 |
| HIV-Ag-8 | 0.697 |
| HIV-Ag-17 | 1.189 |
| HIV-Ag-9 | 1.103 |
| HIV-Ag-18 | 1.179 |

It should be noted that the above embodiments are only used to illustrate the technical solutions of the present disclosure, rather than limiting them. Although the present disclosure has been described in detail with reference to the foregoing embodiments, those skilled in the art should understand that they can modify the technical solutions described in the foregoing embodiments, or replace some or all of the technical features equivalently; and these modifications or replacements do not deviate the essence of the corresponding technical solutions from the scope of the technical solutions of the embodiments of the present disclosure.

INDUSTRIAL APPLICABILITY

The specific peptides of the present disclosure allow better detection of anti-HIV-1 antibodies and better avoid potential "false negative" as well as "false positive" results. The detection method using the synthetic peptide provided by the present disclosure has high sensitivity and specificity of 100% and more than 99.75%, respectively. The specific peptides of the present disclosure, due to their high sensitivity and specificity, are useful for the early diagnosis of HIV-1 infection.

What is claimed is:

1. A synthetic peptide, comprising an amino acid sequence set forth as SEQ ID NO: 1, the synthetic peptide comprising the following mutations:
   T77, replaced by V, N or S;
   N101, replaced by D, E or Q;
   G105, replaced by K, H or R;
   P124, replaced by D or E; and
   K127, replaced by D, E or Q.

2. The synthetic peptide according to claim 1, wherein the synthetic peptide further comprises at least one of the following mutations:
   R18, replaced by S;
   Q95, replaced by E;
   L106, replaced by E;
   L123, replaced by K; or
   N130, replaced by K.

3. The synthetic peptide according to claim 1, wherein the synthetic peptide is labeled with an indicator for displaying signal strength.

4. An isolated nucleic acid molecule, encoding the synthetic peptide according to claim 1.

5. A vector, comprising the nucleic acid molecule according to claim 4.

6. A host cell, transformed with the vector according to claim 5.

7. A method for producing a peptide comprising: expressing the nucleic acid molecule of claim 4, and isolating the peptide produced.

8. A kit, comprising the synthetic peptide according to claim 1.

9. The synthetic peptide according to claim 3, wherein the indicator for displaying signal strength comprises any one of fluorescent substance, quantum dot, digoxigenin-labeled probe, biotin, radioisotope, radioactive contrast agent, paramagnetic ion fluorescent microsphere, electron dense substance, chemiluminescent label, ultrasound contrast agent, photosensitizer, colloidal gold, or enzyme.

10. The synthetic peptide according to claim 1, wherein the synthetic peptide is coupled to a solid-phase substrate.

11. The synthetic peptide according to claim 10, wherein the solid-phase substrate is a microtiter plate or a polystyrene plate.

12. The synthetic peptide according to claim 1, wherein the synthetic peptide is selected from HIV-Ag-1 to HIV-Ag-18, wherein
   HIV-Ag-1 represents an amino acid sequence set forth as SEQ ID NO: 1 containing mutation sites: T77 replaced by V, N101 replaced by E, G105 replaced by K, P124 replaced by D, and K127 replaced by D;
   HIV-Ag-2 represents an amino acid sequence set forth as SEQ ID NO: 1 containing mutation sites: T77 replaced by N, N101 replaced by D, G105 replaced by H, P124 replaced by E, and K127 replaced by E;

HIV-Ag-3 represents an amino acid sequence set forth as SEQ ID NO: 1 containing mutation sites: T77 replaced by S, N101 replaced by Q, G105 replaced by R, P124 replaced by D, and K127 replaced by Q;

HIV-Ag-4 represents an amino acid sequence set forth as SEQ ID NO: 1 containing mutation sites: T77 replaced by S, N101 replaced by D, G105 replaced by R, P124 replaced by E, and K127 replaced by E;

HIV-Ag-5 represents an amino acid sequence set forth as SEQ ID NO: 1 containing mutation sites: T77 replaced by V, N101 replaced by D, G105 replaced by K, P124 replaced by E, and K127 replaced by D;

HIV-Ag-6 represents an amino acid sequence set forth as SEQ ID NO: 1 containing mutation sites: T77 replaced by N, N101 replaced by E, G105 replaced by H, P124 replaced by D, and K127 replaced by E;

HIV-Ag-7 represents an amino acid sequence set forth as SEQ ID NO: 1 containing mutation sites: T77 replaced by V, N101 replaced by Q, G105 replaced by R, P124 replaced by D, and K127 replaced by Q;

HIV-Ag-8 represents an amino acid sequence set forth as SEQ ID NO: 1 containing mutation sites: T77 replaced by S, N101 replaced by Q, G105 replaced by K, P124 replaced by E, and K127 replaced by D;

HIV-Ag-9 represents an amino acid sequence set forth as SEQ ID NO: 1 containing mutation sites: T77 replaced by N, N101 replaced by Q, G105 replaced by H, P124 replaced by E, and K127 replaced by Q;

HIV-Ag-10 represents an amino acid sequence set forth as SEQ ID NO: 1 containing mutation sites: T77 replaced by V, N101 replaced by E, G105 replaced by K, P124 replaced by D, K127 replaced by D, R18 replaced by S, Q95 replaced by E, L106 replaced by E, L123 replaced by K, and N130 replaced by K;

HIV-Ag-11 represents an amino acid sequence set forth as SEQ ID NO: 1 containing mutation sites: T77 replaced by N, N101 replaced by D, G105 replaced by H, P124 replaced by E, K127 replaced by E, R18 replaced by S, Q95 replaced by E, L106 replaced by E, L123 replaced by K, and N130 replaced by K;

HIV-Ag-12 represents an amino acid sequence set forth as SEQ ID NO: 1 containing mutation sites: T77 replaced by S, N101 replaced by Q, G105 replaced by R, P124 replaced by D, K127 replaced by Q, R18 replaced by S, Q95 replaced by E, L106 replaced by E, L123 replaced by K, and N130 replaced by K;

HIV-Ag-13 represents an amino acid sequence set forth as SEQ ID NO: 1 containing mutation sites: T77 replaced by S, N101 replaced by D, G105 replaced by R, P124 replaced by E, K127 replaced by E, R18 replaced by S, Q95 replaced by E, L106 replaced by E, L123 replaced by K, and N130 replaced by K;

HIV-Ag-14 represents an amino acid sequence set forth as SEQ ID NO: 1 containing mutation sites: T77 replaced by V, N101 replaced by D, G105 replaced by K, P124 replaced by E, K127 replaced by D, R18 replaced by S, Q95 replaced by E, L106 replaced by E, L123 replaced by K, and N130 replaced by K;

HIV-Ag-15 represents an amino acid sequence set forth as SEQ ID NO: 1 containing mutation sites: T77 replaced by N, N101 replaced by E, G105 replaced by H, P124 replaced by D, K127 replaced by E, R18 replaced by S, Q95 replaced by E, L106 replaced by E, L123 replaced by K, and N130 replaced by K;

HIV-Ag-16 represents an amino acid sequence set forth as SEQ ID NO: 1 containing mutation sites: T77 replaced by V, N101 replaced by Q, G105 replaced by R, P124 replaced by D, K127 replaced by Q, R18 replaced by S, Q95 replaced by E, L106 replaced by E, L123 replaced by K, and N130 replaced by K;

HIV-Ag-17 represents an amino acid sequence set forth as SEQ ID NO: 1 containing mutation sites: T77 replaced by S, N101 replaced by Q, G105 replaced by K, P124 replaced by E, K127 replaced by D, R18 replaced by S, Q95 replaced by E, L106 replaced by E, L123 replaced by K, and N130 replaced by K; and HIV-Ag-18 represents an amino acid sequence set forth as SEQ ID NO: 1 containing mutation sites: T77 replaced by N, N101 replaced by Q, G105 replaced by H, P124 replaced by E, K127 replaced by Q, R18 replaced by S, Q95 replaced by E, L106 replaced by E, L123 replaced by K, and N130 replaced by K.

13. The kit according to claim 8, further comprising one or more of an immunologically acceptable diluent, a buffer, a protease inhibitor, or a blocking agent for blocking non-specific binding of antibodies.

\* \* \* \* \*

SEQUENCE LISTING

<160> NUMBER OF SEQ ID NOS: 1

<210> SEQ ID NO 1
<211> LENGTH: 139
<212> TYPE: PRT
<213> ORGANISM: Human Immunodeficiency Virus

<400> SEQUENCE: 1

Thr Leu Thr Val Gln Ala Arg Gln Leu Leu Ser Gly Ile Val Gln Gln
1               5                   10                  15

Gln Arg Asn Leu Leu Arg Ala Ile Glu Ala Gln Gln His Leu Leu Gln
            20                  25                  30

Leu Thr Val Trp Gly Ile Lys Gln Leu Gln Ala Arg Val Leu Ala Val
        35                  40                  45

Glu Arg Tyr Leu Lys Asp Gln Gln Leu Leu Gly Ile Trp Gly Cys Ser
    50                  55                  60

Gly Lys Leu Ile Cys Thr Thr Ala Val Pro Trp Asn Thr Ser Trp Ser
65                  70                  75                  80

Asn Lys Ser Leu Ser Glu Ile Trp Asp Asn Met Thr Trp Met Gln Trp
                85                  90                  95

Glu Arg Glu Ile Asn Asn Tyr Thr Gly Leu Ile Tyr Thr Leu Ile Glu
            100                 105                 110

Glu Ser Gln Asn Gln Gln Glu Lys Asn Glu Leu Pro Leu Leu Lys Leu
            115                 120                 125

Asp Asn Trp Ala Ser Leu Trp Asn Trp Phe Asp
            130                 135